United States Patent
Nakanishi et al.

(10) Patent No.: US 9,404,874 B2
(45) Date of Patent: Aug. 2, 2016

(54) INSPECTION APPARATUS AND INSPECTION METHOD

(71) Applicants: SCREEN Holdings Co., Ltd., Kyoto (JP); OSAKA UNIVERSITY, Osaka (JP)

(72) Inventors: Hidetoshi Nakanishi, Kyoto (JP); Akira Ito, Kyoto (JP); Iwao Kawayama, Osaka (JP); Masayoshi Tonouchi, Osaka (JP)

(73) Assignee: SCREEN HOLDINGS, CO., LTD., Kyoto (JP)

( * ) Notice: Subject to any disclaimer, the term of this patent is extended or adjusted under 35 U.S.C. 154(b) by 0 days.

(21) Appl. No.: 14/667,648

(22) Filed: Mar. 24, 2015

(65) Prior Publication Data
US 2015/0276607 A1 Oct. 1, 2015

(30) Foreign Application Priority Data

Mar. 25, 2014 (JP) .................. 2014-061679

(51) Int. Cl.
*G01N 21/64* (2006.01)
*G01N 21/95* (2006.01)

(52) U.S. Cl.
CPC ........ *G01N 21/9501* (2013.01); *G01N 21/6489* (2013.01); *G01N 2201/0697* (2013.01); *G01N 2201/06113* (2013.01); *G01N 2201/10* (2013.01)

(58) Field of Classification Search
CPC .................. G01N 21/6489; G01N 21/9501
See application file for complete search history.

(56) References Cited

U.S. PATENT DOCUMENTS

| | | | |
|---|---|---|---|
| 6,081,127 A * | 6/2000 | Wagner et al. | 324/754.23 |
| 8,129,683 B2 | 3/2012 | Itsuji et al. | |
| 8,872,114 B2 | 10/2014 | Nakanishi et al. | |
| 2006/0006886 A1* | 1/2006 | Yamashita et al. | 324/751 |
| 2013/0146787 A1* | 6/2013 | Giesecke | 250/459.1 |

FOREIGN PATENT DOCUMENTS

| | | |
|---|---|---|
| JP | 2008-224432 A | 9/2008 |
| JP | 2009-175127 A | 8/2009 |
| JP | 2013-019861 A | 1/2013 |

OTHER PUBLICATIONS

Johnston et al., "Temperature-dependent photoluminescence imaging and characterization of a multi-cystalline silicon solar cell defect area," 2011, 37th IEEE Photovoltaic Specialists Confereence, pp. 000069-000074.*

* cited by examiner

*Primary Examiner* — Kiho Kim
(74) *Attorney, Agent, or Firm* — McDermott Will & Emery LLP

(57) ABSTRACT

An inspection apparatus according to an aspect of the present invention inspects a solar cell that is of a photo device. The inspection apparatus includes: an irradiation part that irradiates the solar cell with pulse light emitted from a femtosecond laser that is of a light source; an electromagnetic wave detection part that detects an electromagnetic wave pulse emitted from the solar cell in response to the irradiation of the solar cell with the pulse light; and a PL light detection part that detects photoluminescence light generated in the solar cell in response to the irradiation of the solar cell with the pulse light.

12 Claims, 13 Drawing Sheets

F I G. 7
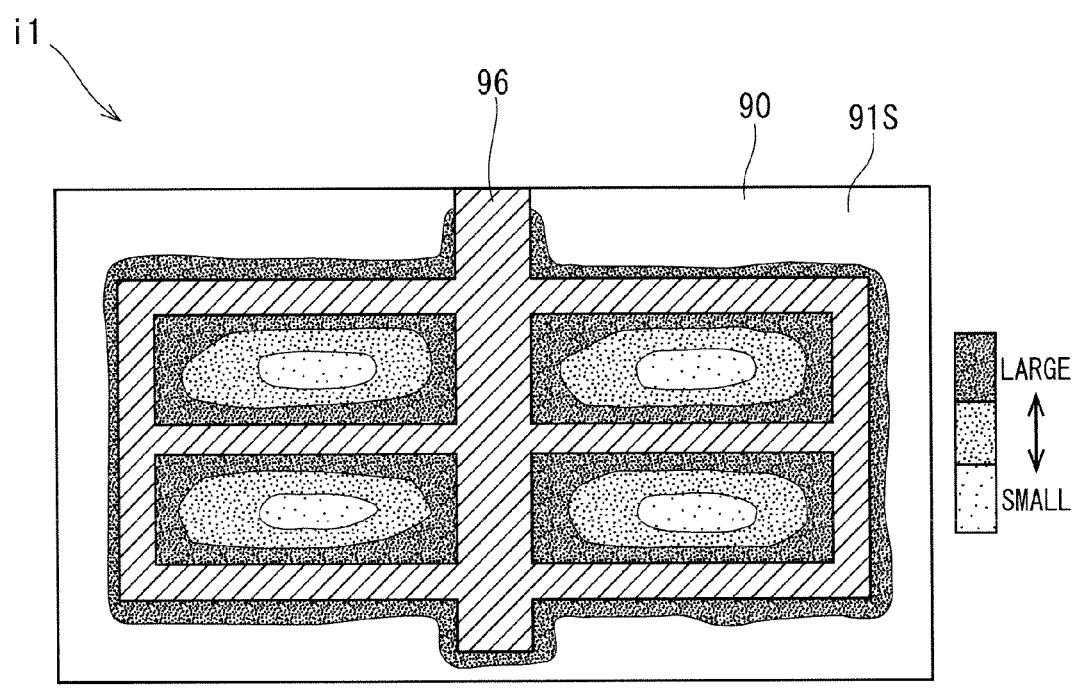

INSPECTION APPARATUS AND INSPECTION METHOD

RELATED APPLICATIONS

This application claims the benefit of Japanese Application No. 2014-061679, filed on Mar. 25, 2014, the disclosures of which Applications are incorporated by reference herein.

BACKGROUND OF THE INVENTION

1. Field of the Invention

The present invention relates to a technology of inspecting a semiconductor device or a photo device.

2. Description of the Background Art

Some technologies of inspecting the semiconductor device or the photo device have been proposed (for example, see Japanese Patent Application Laid-Open Nos. 2008-224432 and 2013-019861).

In Japanese Patent Application Laid-Open No. 2008-224432, a solar cell that is of the photo device is irradiated with LED light having a specific emission wavelength to emit photoluminescence light (hereinafter referred to as PL light) from the solar cell. The solar cell is inspected by detecting the emitted PL light. In Japanese Patent Application Laid-Open No. 2013-019861, the solar cell that is of the photo device is irradiated with pulse light to emit an electromagnetic wave. The photo device is inspected by detecting an emitted electromagnetic wave pulse.

In order to obtain more information on an inspection object, desirably the PL light and the electromagnetic wave can be inspected with an identical apparatus. However, in Japanese Patent Application Laid-Open No. 2008-224432, an LED (continuous light) is used as a light source, and a whole surface of the solar cell is irradiated with the LED. On the other hand, in Japanese Patent Application Laid-Open No. 2013-019861, pulse light is used as the light source (specifically, a femtosecond laser), and the solar cell is irradiated with the spot-shape pulse light. That is, conventionally, the PL light differs from the electromagnetic wave in the light source and an irradiation mode. Therefore, in the case that a system that generates the PL light and a system that generates the electromagnetic wave are simply combined, two irradiation devices are required in one apparatus, which leads to a cost increase and enlargement of the apparatus.

SUMMARY OF THE INVENTION

The present invention is aimed at an inspection apparatus that inspects an inspection object including a semiconductor device or a photo device.

According to one aspect of the present invention, an inspection apparatus includes: an irradiation part that irradiates the inspection object with pulse light emitted from a light source; an electromagnetic wave detection part that detects an electromagnetic wave emitted from the inspection object in response to the irradiation of the inspection object with the pulse light; and a PL light detection part that detects photoluminescence light emitted from the inspection object in response to the irradiation of the inspection object with the pulse light generating the electromagnetic wave from the inspection object.

The electromagnetic wave and photoluminescence light (PL light) that are emitted from the inspection object can be detected using the identical light source. Therefore, the inspection can be performed based on the electromagnetic wave and the PL light while a cost increase and enlargement of the apparatus are constrained.

Preferably the pulse light is light that can reach a portion deeper than a depletion layer formed in the inspection object.

The photocarrier can be excited in the portion deeper than the depletion layer. Therefore, the depletion layer can be inspected based on the detected electromagnetic wave, and the portion deeper than the depletion layer can be inspected in the inspection object based on the detected PL light.

The pulse light is the light absorbed by the depletion layer formed in the inspection object.

The pulse light is absorbed by the depletion layer, which allows the photocarrier to be generated in the portion shallower than the depletion layer. Therefore, the depletion layer can be inspected based on the detected electromagnetic wave, and the portion shallower than the depletion layer can be inspected based on the detected PL light.

Preferably the inspection apparatus further includes a scanning mechanism that scans an inspection object area in the inspection object with the pulse light.

The electromagnetic wave or the PL light can be generated by efficiently irradiating the inspection object area with the pulse light.

Preferably the inspection apparatus further includes an electromagnetic wave intensity distribution image generation part that generates an electromagnetic wave intensity distribution image indicating an intensity distribution of the electromagnetic wave generated in the inspection object area.

The electromagnetic wave intensity distribution can visually be understood. Therefore, a defect region can easily be identified.

Preferably the inspection apparatus further includes a time waveform restoration part that restores a time waveform of the electromagnetic wave based on an electric field intensity of the electromagnetic wave detected by operating a delay part. At this point, the light source is a femtosecond laser, and the detection part includes: a detector that detects an electric field intensity of the electromagnetic wave by receiving probe light emitted from the femtosecond laser; and the delay part that that delays a time the probe light is incident to the detector relative to a time the electromagnetic wave is incident to the detector.

The time waveform of the electromagnetic wave can be restored, so that a characteristic of the inspection object can more particularly be analyzed.

Preferably the inspection apparatus further includes an inspection position setting part that sets a position where the irradiation part irradiates the inspection object with the pulse light in order to restore the time waveform.

The relatively time-consuming inspection that restores the electromagnetic wave is performed only at the setting position, so that the efficient inspection can be achieved.

Preferably the inspection apparatus further includes a PL light intensity distribution image generation part that generates a PL light intensity distribution image indicating an intensity distribution of the photoluminescence light generated in the inspection object area.

The PL light intensity distribution can visually be understood. Therefore, a defect region can easily be identified.

Preferably the inspection apparatus further includes: an electromagnetic wave intensity distribution image generation part that generates an electromagnetic wave intensity distribution image indicating an intensity distribution of the electromagnetic wave generated in the inspection object area; and an image synthesis part that synthesizes the PL light intensity distribution image and the electromagnetic wave intensity distribution image.

The synthetic image in which the electromagnetic wave intensity distribution and the PL light intensity distribution are simultaneously understood can be obtained.

Preferably the inspection apparatus further includes a determination part that determines whether an intensity of the photoluminescence light detected by the PL light detection part satisfies a predetermined reference value. At this point, the scanning mechanism scans an area where the reference value is not satisfied with the pulse light, and the electromagnetic wave detection part detects an electromagnetic wave generated by the scan.

Because the relatively time-consuming detection of the electromagnetic wave can be performed while the area is restricted, the efficient inspection can be achieved.

The present invention is aimed at an inspection method for inspecting an inspection object including a semiconductor device or a photo device.

According to one aspect of the present invention, an inspection method includes the steps of: (a) irradiating the inspection object with pulse light emitted from a light source; (b) detecting an electromagnetic wave emitted from the inspection object in response to the irradiation of the inspection object with the pulse light; and (c) detecting photoluminescence light emitted from the inspection object in response to the irradiation of the inspection object with the pulse light generating the electromagnetic wave from the inspection object.

The electromagnetic wave and photoluminescence light (PL light) that are emitted from the inspection object can be detected using the identical light source. Therefore, the inspection can be performed based on the electromagnetic wave and the PL light while an increase of an inspection cost and enlargement of an inspection areas are constrained.

Preferably the step (a) includes (a-1) a step of scanning an inspection object area of the inspection object with the pulse light.

Therefore, an object of the present invention is to provide a technology of constraining the cost increase and the enlargement of the apparatus detecting the electromagnetic wave and PL light that are emitted from the inspection object.

These and other objects, features, aspects and advantages of the present invention will become more apparent from the following detailed description of the present invention when taken in conjunction with the accompanying drawings.

BRIEF DESCRIPTION OF THE DRAWINGS

FIG. 7 is a view illustrating an electromagnetic wave intensity distribution image;

DESCRIPTION OF THE PREFERRED EMBODIMENTS

Figure 1:
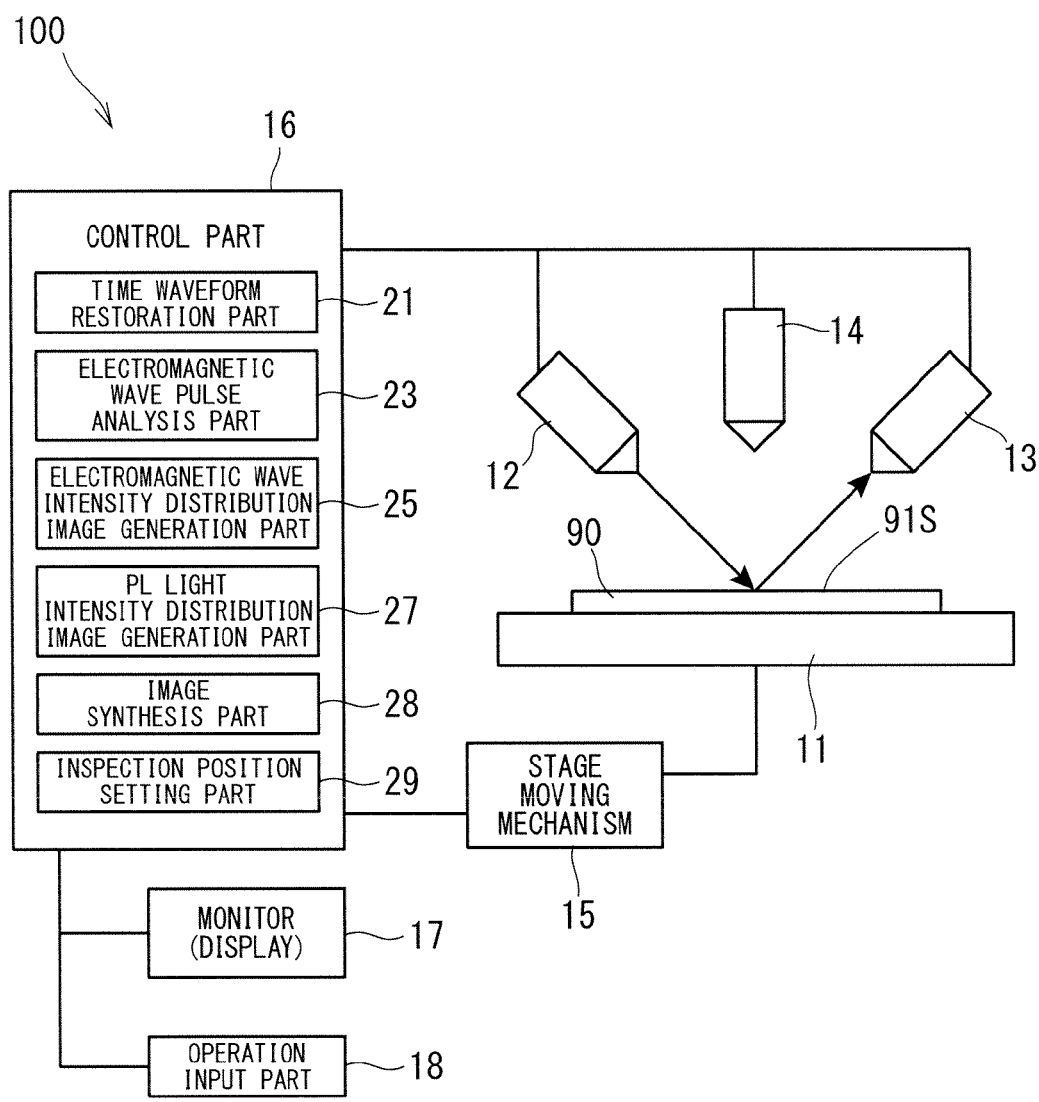
FIG. 1 is a schematic diagram illustrating a configuration of a photo device inspection apparatus according to a first preferred embodiment.

Hereinafter, preferred embodiments of the present invention will be described below with reference to the accompanying drawings. In the drawings, for the sake of easy understanding, a size of each unit or the number of units is exaggerated or simplified as needed basis.

Figure 2:
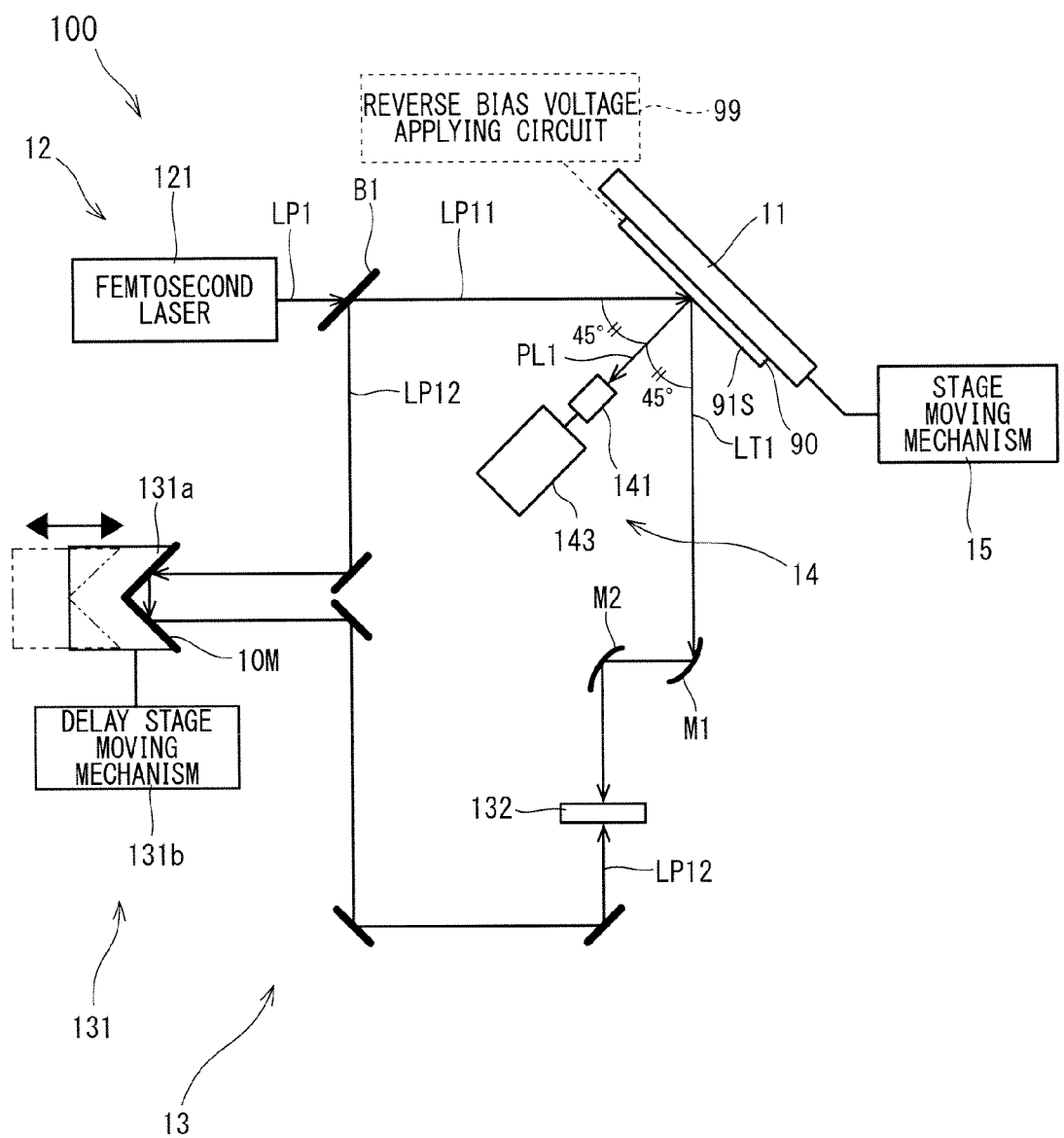
FIG. 2 is a schematic diagram illustrating configurations of an irradiation part, an electromagnetic wave detection part, and a PL light detection part of the photo device inspection apparatus in FIG. 1.

1. First Preferred Embodiment 1.1. Configuration and Function of Photo Device Inspection Apparatus FIG. 1 is a schematic diagram illustrating a configuration of an inspection apparatus 100 according to a first preferred embodiment. FIG. 2 is a schematic diagram illustrating configurations of an irradiation part 12, an electromagnetic wave detection part 13, and a PL light detection part 14 of the inspection apparatus 100 in FIG. 1.

The inspection apparatus 100 is configured to suit a characteristic inspection of a solar cell 90 that is a kind of substrate on which the photo device is formed. The photo device such as the solar cell includes a pn-junction in which, for example, a p-type semiconductor and an n-type semiconductor are joined to each other. Near the pn-junction, electrons and holes diffuse and unit with each other to generate a diffusion current, thereby forming a depletion layer in which the electrons and the holes hardly exist. In the depletion layer, because a force pulling back the electrons and the holes to an n-type region and a p-type region is generated, an electric field (internal electric field) is generated in the photo device.

At this point, in the case that the pn-junction is irradiated with light having energy exceeding a bandgap, the internal electric field moves free electrons generated in the pn-junction onto an n-type semiconductor side, and moves remaining free holes generated in the pn-junction onto a p-type semiconductor side. In the photo device, this current is taken out to an outside through electrodes attached to the n-type semiconductor and the p-type semiconductor. For example, in the solar cell, the movement of the free electrons and free holes that are generated by irradiating the depletion layer of the pn-junction with the light is used as a DC current.

An electromagnetic wave pulse having a specific wavelength is generated when the photo device is irradiated with pulse light having a predetermined wavelength. According to a Maxwell's equation, when a current changes, an electromagnetic wave having an intensity proportional to time differentiation of the current is generated. That is, the generation and disappearance of a photocurrent happen instantaneously by irradiating a photoexcited carrier generation region such as the depletion layer with the pulse light. The electromagnetic wave pulse is generated in proportion to the time differentiation of the instantaneously-generated photocurrent.

The generation of the photocurrent reflects a characteristic of the photoexcited carrier generation region such as the depletion layer. Accordingly, the characteristic of the photoexcited carrier generation region such as the depletion layer can be inspected by analyzing the generated electromagnetic wave pulse. Based on the above principle, the inspection apparatus 100 is configured to detect the electromagnetic wave pulse that is generated when the solar cell 90 is irradiated with the pulse light having the predetermined wavelength.

As illustrated in FIG. 1, the inspection apparatus 100 includes a stage 11, the irradiation part 12, the electromagnetic wave detection part 13, the PL light detection part 14, a stage moving mechanism 15, a control part 16, a monitor 17, and a operation input part 18.

The solar cell 90 is held on the stage 11 by required fixing means. Examples of the fixing means include means in which a clipping tool clipping a substrate is used, an adhesive sheet, and a suction hole formed in a surface of the stage 11. Alternatively, any fixing means may be used as long as the solar cell 90 can be fixed. In the first preferred embodiment, the solar cell 90 is held on the stage 11 such that the irradiation part 12 and the electromagnetic wave detection part 13 are arranged on a side of a light receiving surface 91S of the solar cell 90.

As illustrated in FIG. 2, the irradiation part 12 includes a femtosecond laser 121. For example, the femtosecond laser 121 emits pulse light (pulse light LP1) having a wavelength including visible light regions of 360 nm (nanometer) to 1.5 µm (micrometer). Specifically, the femtosecond laser 121 emits the linearly-polarized pulse light having a center wavelength of around 800 nm, periods of several kilohertz to several gigahertz, and pulse widths of about 10 femtosecond to about 150 femtosecond. Alternatively, the femtosecond laser 121 may emit the pulse light having another wavelength region (for example, visible light wavelength such as a blue wavelength (450 nm to 495 nm) and a green wavelength (495 nm to 570 nm)).

The pulse light LP1 emitted from the femtosecond laser 121 is split into two by a beam splitter B1. The solar cell 90 is irradiated with one of the two pieces of split pulse light (pulse light LP11). At this point, the irradiation part 12 irradiates the solar cell 90 with the pulse light LP11 from the side of the light receiving surface 91S. The solar cell 90 is irradiated with the pulse light LP11 such that an optical axis of the pulse light LP11 is obliquely incident to the light receiving surface 91S of the solar cell 90. In the first preferred embodiment, an irradiation angle is set such that an incident angle becomes 45 degrees. However, the incident angle is not limited to 45 degrees, but the incident angle can be properly changed within a range of 0 degree to 90 degrees.

Figure 3:
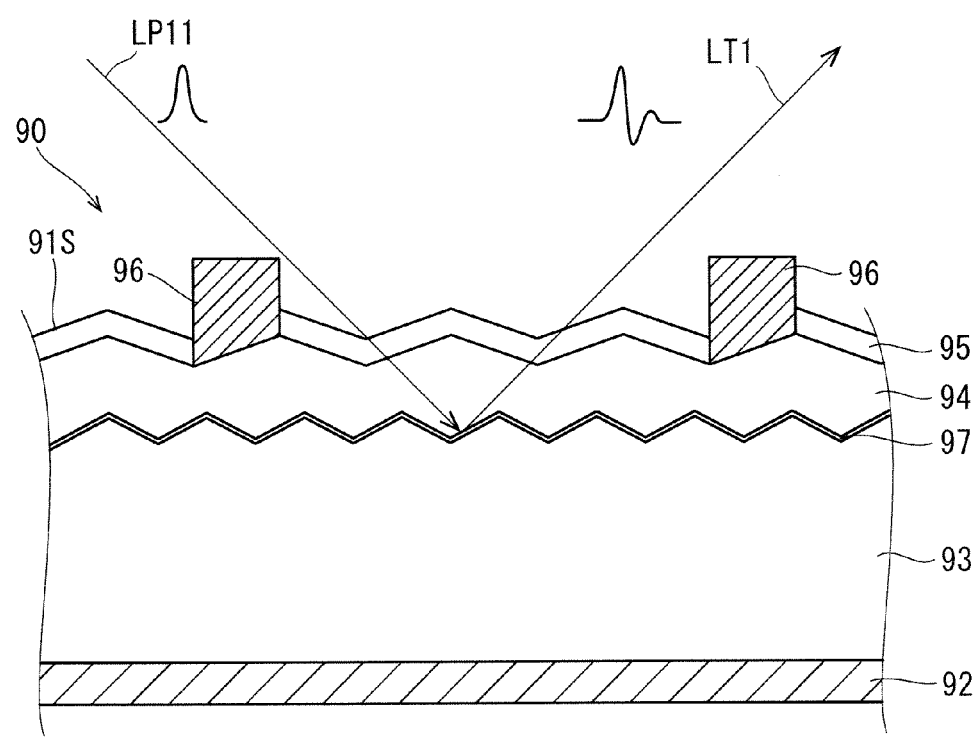
FIG. 3 is a schematic sectional view of a solar cell.
Figure 4:
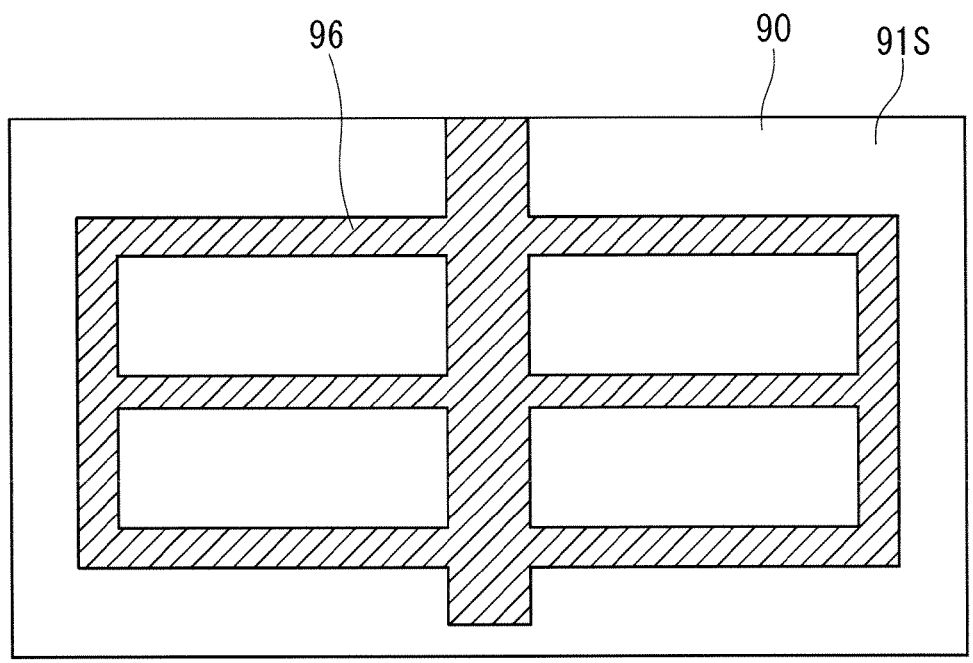
FIG. 4 is a plan view of the solar cell when the solar cell is viewed from a light receiving surface side.
Figure 5:
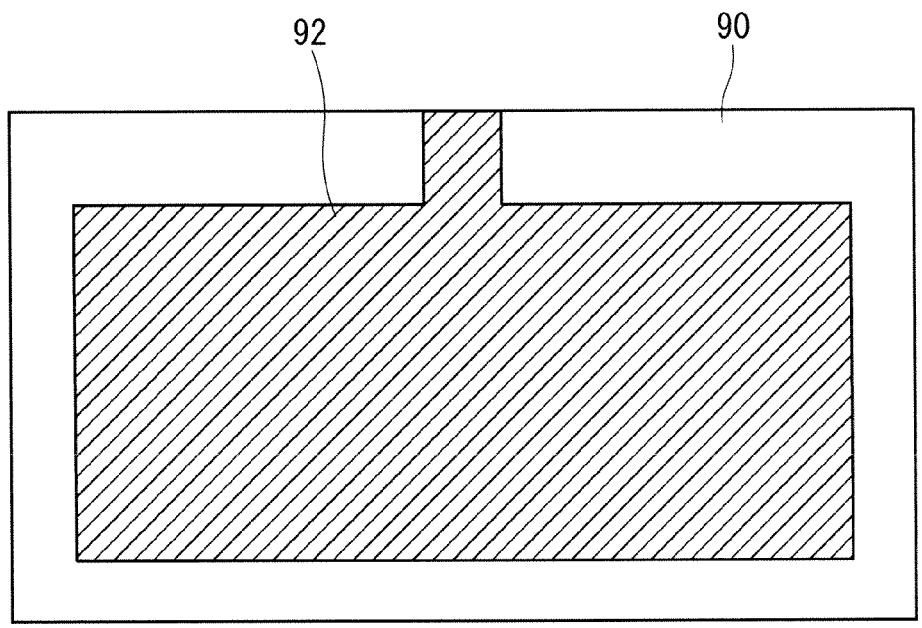
FIG. 5 is a plan view of the solar cell when the solar cell is viewed from a back side.

FIG. 3 is a schematic sectional view of the solar cell 90. FIG. 4 is a plan view of the solar cell 90 when the solar cell 90 is viewed from the side of the light receiving surface 91S. FIG. 5 is a plan view of the solar cell 90 when the solar cell 90 is viewed from a back side. The solar cell 90 is constructed as a crystalline silicon solar cell. The solar cell 90 is constructed as the crystalline silicon solar cell having a stacking structure. The stacking structure includes a plate-shape backside electrode 92 made of such as aluminum, a p-type silicon layer 93, an n-type silicon layer 94, an anti-reflection film 95, and a lattice-shape light receiving surface electrode 96 in the ascending order. The anti-reflection film 95 is made of oxide silicon, nitride silicon, or oxide titanium, and the like.

In principal surfaces of the solar cell 90, the principal surface on the side on which the light receiving surface electrode 96 is provided constitutes the light receiving surface 91S. That is, the solar cell 90 is designed to generate power by receiving the light from the side of the light receiving surface 91S. A transparent electrode may be used as the light receiving surface electrode 96. The inspection apparatus 100 may be applied to the inspection of a solar cell (such as an amorphous silicon solar cell) other than the crystalline silicon solar cell. For the amorphous silicon solar cell, generally energy gaps of 1.75 eV to 1.8 eV are larger than an energy gap of 1.2 eV of the crystalline silicon solar cell. In such cases, a terahertz wave can well be generated in the amorphous silicon solar cell by setting the wavelength of the femtosecond laser 121 to, for example, 700 µm or less. The inspection apparatus 100 can also be applied to other semiconductor solar cell (such as a CIGS solar cell and a GaAs solar cell) with a similar way of thinking.

The light receiving surface 91S of the solar cell 90 has a required texture structure in order to constrain a reflection loss of the light. Specifically, irregularities of several micrometers to several tens micrometers are formed by anisotropic etching, or V-shape grooves are formed by a mechanical method. Generally the light receiving surface 91S of the solar cell 90 is formed to let in light as efficient as possible. Accordingly, when the solar cell 90 is irradiated with the pulse light having the predetermined wavelength, the pulse light easily reaches at a pn-junction 97. For example, in the solar cell 90, light mainly having the visible light wavelength region of wavelengths of 1 µm or less can easily reach the pn-junction 97. Thus, an electromagnetic wave pulse LT1 can well be generated, when the solar cell 90 is placed on the inspection apparatus 100 such that the principal surface on the light receiving side in a use state constitutes the light receiving surface 91S of the pulse light LP11.

A junction portion between the p-type silicon layer 93 and the n-type silicon layer 94 constitutes the pn-junction 97 in which the depletion layer is formed. The electromagnetic wave pulse is generated by irradiating the pn-junction 97 with the pulse light LP11, and the electromagnetic wave pulse is emitted to the outside. In the first preferred embodiment, the electromagnetic wave pulse detected by the electromagnetic wave detection part 13 is an electromagnetic wave pulse (hereinafter referred to as the electromagnetic wave pulse LT1) of a terahertz region (frequencies of 0.01 THz to 10 THz).

In the inspection apparatus 100, the inspection object substrate is not limited to the solar cell 90. Other photo devices or other semiconductor devices can become the inspection object. As used herein, the photo device means electronic devices, such as a photodiode, image sensors such as a CMOS sensor and a CCD sensor, a solar cell, an LED, and a laser diode, in which a semiconductor photoelectric effect is used. The semiconductor device means such electronic devices except the photo device as a transistor and an integrated circuit (IC and LSI) made of the semiconductor of Si, Ge, or GaAs and a power device in which a resistor or a capacitor and a wide-gap semiconductor are used. The surface of the inspection object is formed flat. Alternatively, the surface of the inspection object may be formed into a curved shape.

In some image sensors, a light receiving element is formed on the back side of the substrate in which the photo device is formed in the use state. Even in this substrate, the electromagnetic wave pulse LT1 can well be detected, when the image sensor is placed on the inspection apparatus 100 such that the principal surface on the light receiving side in the use state constitutes the light receiving surface.

Referring to FIG. 2, the other piece of pulse light split by the beam splitter B1 is incident as probe light LP12 to a detector 132 through a delay part 131 and a mirror. The electromagnetic wave pulse LT1 generated in response to the irradiation with the pulse light LP11 is collected by parabolic mirrors M1 and M2, and is incident to the detector 132.

For example, the detector 132 includes a photoconductive switch as an electromagnetic wave detection element. When the detector 132 is irradiated with the probe light LP12 while the electromagnetic wave pulse is incident to the detector 132, the current is instantaneously generated in the photoconductive switch according to an electric field intensity of the electromagnetic wave pulse LT1. The current generated according to the electric field intensity is converted into a digital quantity through an I/V conversion circuit and an A/D conversion circuit. Thus the electromagnetic wave detection part 13 detects the electric field intensity of the electromagnetic wave pulse LT1 that is generated in the solar cell 90 in response to the irradiation with the probe light LP12. It is conceivable that another element such as a non-linear optical crystal is applied to the detector 132.

The delay part 131 includes a delay stage 131a and a delay stage moving mechanism 131b. The delay part 131 is an optical element that continuously changes an arrival time of the probe light LP12 in a range from the beam splitter B1 to the detector 132. The delay stage 131a is linearly moved along an incident direction of the probe light LP12 by the delay stage moving mechanism 131b. The delay stage 131a includes a turning back mirror 10M that turns back the probe light LP12 in the incident direction.

More particularly, in the delay stage 131a, the turning back mirror 10M is moved by driving the delay stage moving mechanism 131b under the control of the control part 16, thereby precisely changing an optical path length of the probe light LP12. Therefore, the delay stage 131a changes a time difference between the time the electromagnetic wave pulse LT1 reaches the electromagnetic wave detection part 13 (detector 132) and the time the probe light LP12 reaches the electromagnetic wave detection part 13 (detector 132). Accordingly, the delay stage 131a changes the optical path length of the probe light LP12, which allows the electromagnetic wave detection part 13 (detector 132) to delay the time (detection time or sampling time) the electric field intensity of the electromagnetic wave pulse LT1 is detected.

It is also conceivable to change the arrival time of the probe light LP12 at the detector 132. Specifically, an electro-optical effect may be used. That is, an electro-optical element in which a refractive index is changed by changing an applied voltage may be used as the delay element. Specifically, an electro-optical element disclosed in Japanese Patent Application Laid-Open No. 2009-175127 may be used.

Alternatively, the optical path length of the pulse light LP11 (pump light) or the optical path length of the electromagnetic wave pulse LT1 emitted from the solar cell 90 may be changed. In this case, a time the electromagnetic wave pulse LT1 reaches the detector 132 can be shifted relative to the time the probe light LP12 reaches the detector 132. Therefore, the time the detector 132 detects the electric field intensity of the electromagnetic wave pulse LT1 can be delayed.

A reverse bias voltage applying circuit 99 is connected to the solar cell 90 in order to apply a reverse bias voltage between the backside electrode 92 and the light receiving surface electrode 96 during the inspection. A width of the depletion layer of the pn-junction 97 increases by applying the reverse bias voltage between the electrodes, which allows the increase of the internal electric field. Therefore, a quantity of current generated by the pulse light LP11 can be increased.

The electric field intensity of the electromagnetic wave pulse LT1 detected by the detector 132 can be increased, so that detection sensitivity of the electromagnetic wave pulse LT1 can be improved in the detector 132. However, the reverse bias voltage applying circuit 99 may be eliminated.

The PL light detection part 14 includes a spectroscope 141 and a photodetector 143. The photodetector 143 is constructed with a photodiode. The PL light detection part 14 detects photoluminescence light (PL light) PL1 that is generated in the solar cell 90 irradiated with the pulse light LP11 (for example, repetitive frequencies of 80 MHz to 1 GHz). Although the pulse light LP11 with which the solar cell 90 is irradiated can be approximated by continuous light, the pulse light LP11 has the pulse shape. Therefore, exactly the generated PL light PL1 becomes the pulse shape.

In the conventional inspection apparatus (for example, the inspection apparatus disclosed in Japanese Patent Application Laid-Open No. 2008-224432), the whole surface of the inspection object (solar cell) is irradiated with the light. Therefore, it is necessary that the photodetector have a relatively wide detection surface. On the other hand, in the first preferred embodiment, the solar cell 90 is irradiated with the spot-shape pulse light LP11. Therefore, the photodetector 143 has the relatively small detection surface. The photodetector 143 can be constructed with the relatively small number of photodiodes. Therefore, an apparatus cost can be reduced compared with the conventional inspection apparatus.

The light (pulse light LP11) generating the PL light PL1 is the light generating the electromagnetic wave pulse LT1. Both the light generating the PL light PL1 and the light generating the electromagnetic wave pulse LT1 are the light emitted from the femtosecond laser 121 that is of the identical light source.

The PL light is light that is generated when electrons excited by irradiating a substance with light makes a transition to a ground state. This luminous phenomenon is easily affected by an impurity or a defect in the inspection object. The generated light is dispersed into a spectrum and analyzed by the spectroscope 141, whereby information on the impurity or defect in the inspection object can be obtained.

As described above, the electromagnetic wave (terahertz wave) is mainly generated by the pulse light LP11 because of the movement of photocarriers accelerated by the internal electric field of the depletion layer, namely, the electromagnetic wave is generated by the time change in photocurrent. Therefore, the electromagnetic wave differs from the PL light in a generating mechanism. Accordingly, the photo device can more finely be analyzed using a difference of a generating principle.

A bandpass filter may be used in the PL light detection part 14 to exclude the light having the wavelength different from that of the PL light. The bandpass filter may be used instead of the spectroscope 141.

In the case that the wavelength of the pulse light LP emitted from the femtosecond laser 121 is close to the wavelength of the PL light PL1, it is necessary to use the high-precision spectroscope 141 in order to separate the PL light PL1 from the pulse light LP11. At this point, when the pulse light LP11 is converted into the linearly-polarized light to install a polarizer orthogonal to a polarization direction of the pulse light LP11 in front of the spectroscope 141, the pulse light LP11 can be removed in the photodetector 143.

The inspection apparatus 100 may include a CCD camera and an LED or a laser diode as CCD camera that is of a light source for photographing. The CCD camera can be used to photograph an entire image of the solar cell 90 or a position irradiated with the pulse light LP11. Image data acquired by the CCD camera may be transmitted to the control part 16, and displayed on the monitor 17.

The stage moving mechanism 15 includes an X-Y table that moves the stage 11 in a two-dimensional plane. The stage moving mechanism 15 drives the X-Y table to relatively move the solar cell 90 held by the stage 11 with respect to the irradiation part 12. In the inspection apparatus 100, the solar cell 90 can be moved to any position in the two-dimensional plane by the stage moving mechanism 15. In the inspection apparatus 100, a relatively wide range (inspection object area) of the solar cell 90 can be scanned with the pulse light LP11 by the stage moving mechanism 15.

The stage moving mechanism 15 is an example of the scanning mechanism. For example, moving means for moving the irradiation part 12 and the electromagnetic wave detection part 13 in the two-dimensional plane may be provided instead of or in addition to the movement of the solar cell 90. In such cases, each area of the solar cell 90 can be irradiated with the pulse light LP11. It is also conceivable that the inspection object area is scanned with the pulse light LP11 by changing the optical path of the pulse light LP11. Specifically, a galvano-mirror is provided, and the light receiving surface 91S of the solar cell 90 is scanned with the pulse light LP11 in two directions that are parallel to the light receiving surface 91S and orthogonal to each other. A polygon mirror, a piezoelectric mirror, or an acousto-optical element is considered to be used instead of the galvano-mirror. The stage moving mechanism 15 may be eliminated to manually move the stage 11.

The control part 16 has a configuration as a general computer including a CPU, a ROM, a RAM, and an auxiliary storage (for example, a hard disk). The control part 16 is connected to the femtosecond laser 121 of the irradiation part 12, the delay stage 131a and detector 132 of the electromagnetic wave detection part 13, and the stage moving mechanism 15. The control part 16 controls operations of these parts, and receives data from these parts.

More particularly, the control part 16 receives data concerning the electric field intensity of the electromagnetic wave pulse LT1 from the detector 132. The control part 16 controls the delay stage moving mechanism 131b moving the delay stage 131a. The control part 16 receives data concerning the position of the delay stage 131a, for example, a moving distance of the turning back mirror 10M from a linear scale provided in the delay stage 131a.

The control part 16 includes a time waveform restoration part 21, an electromagnetic wave pulse analysis part 23, an electromagnetic wave intensity distribution image generation part 25, a PL light intensity distribution image generation part 27, an image synthesis part 28, and an inspection position setting part 29. These processing parts are functions that are implemented in a manner such that the CPU operates according to a program. Alternatively, a part or all the processing parts may be implemented in a hardware manner by a dedicated calculation circuit.

Based on the electric field intensity detected by the electromagnetic wave detection part 13 (detector 132), the time waveform restoration part 21 restores a time waveform of the electromagnetic wave pulse LT1 with respect to the electromagnetic wave pulse LT1 generated in the solar cell 90. Specifically, the time waveform restoration part 21 moves the turning back mirror 10M of the delay stage 131a to change the optical path length (the optical path length of a first optical path) of the probe light LP12, thereby changing the time the probe light LP12 reaches the detector 132. Therefore, the time (phase) the electric field intensity of the electromagnetic wave pulse LT1 is detected in the detector 132 is changed. The time waveform restoration part 21 detects the electric field intensity of the electromagnetic wave pulse LT1 in each different phase, and plots the detected electric field intensity along a time axis. Therefore, the time waveform restoration part 21 restores the time waveform of the electromagnetic wave pulse LT1.

The electromagnetic wave pulse analysis part 23 analyzes the time waveform restored by the time waveform restoration part 21. The electromagnetic wave pulse analysis part 23 detects a peak of the electric field intensity or analyzes the frequency by a Fourier transform with respect to the time waveform of the electromagnetic wave pulse LT1 restored by the time waveform restoration part 21. Therefore, the characteristic of the solar cell 90 is analyzed based on the electromagnetic wave pulse.

The electromagnetic wave intensity distribution image generation part 25 generates an electromagnetic wave intensity distribution image with respect to the inspection object area (part or whole of the solar cell 90) of the solar cell 90. The electromagnetic wave intensity distribution image is an image in which a distribution of the electric field intensity of the electromagnetic wave pulse LT1 emitted in response to the irradiation of the solar cell 90 with the pulse light LP11 is visualized. The electromagnetic wave intensity distribution image is an image in which a color or a pattern is added to each place irradiated with the pulse light LP11 according to the detected electric field intensity of the electromagnetic wave pulse LT1.

The PL light intensity distribution image generation part 27 generates a PL light intensity distribution image with respect to the inspection object area of the solar cell 90. The PL light intensity distribution image is an image in which an intensity distribution of the PL light PL1 emitted from the solar cell 90 in response to the irradiation of the solar cell 90 with the pulse light LP11 is visualized. The PL light intensity distribution image is an image in which the color or the pattern is added to each place irradiated with the pulse light LP11 according to the detected intensity of the PL light.

The image synthesis part 28 generates a new synthetic image including information on the electromagnetic wave intensity distribution and information on the PL light intensity distribution by a pixel calculation from the electromagnetic wave intensity distribution image generated by the electromagnetic wave intensity distribution image generation part 25 and the PL light image generated by the PL light intensity distribution image generation part 27.

For example, in the case that the synthetic image is a differential image between the electromagnetic wave intensity distribution image and the PL light image, the place where one of the emission of the electromagnetic wave and the generation of the PL light is abnormal can easily be identified from the synthetic image.

A relationship between the wavelength of the light and an approach length to the inspection object will be described below. It is assumed that the light having intensity of I0 is incident to the inspection object. Assuming that α is a light absorption coefficient, an intensity I(x) of the light is expressed by the following equation (1) when the light travels in the inspection object by x (cm).

$$I(x) = I_0 \cdot e^{-\alpha x} \quad \text{equation (1)}$$

For example, for $\alpha = 10^4$ cm$^{-1}$, the light is attenuated to $1/e = 0.37$ of the incident light when the light proceeds by $x = 1/\alpha = 10^{-4}$ (cm). For example, for a thickness of 3 μm, the light intensity becomes 5% or less. The light absorption coefficient α depends on the substance and the wavelength. Therefore, an invasion depth of the light having the specific wavelength in the inspection object can be specified when a material of the inspection object is well known.

Specifically, in the solar cell 90 of FIG. 3, it is assumed that the n-type silicon layer 94 having the thickness of 0.3 μm is made of crystalline silicon. It is considered that the solar cell 90 is irradiated with the 365 nm or 500 nm pulse light LP11.

For the wavelength of 365 nm, the crystalline silicon has the light absorption coefficient α of 10 (cm$^{-1}$). Therefore, transmittance $I(x)/I_0$ becomes 0.05 when the pulse light LP11 proceeds by 0.3 μm. That is, 95% of the pulse light LP11 is absorbed by the n-type silicon layer 94, but the pulse light LP11 can hardly reach the p-type silicon layer 93.

On the other hand, for the wavelength of 500 nm, the crystalline silicon has the light absorption coefficient α of $10^4$ (cm$^{-1}$). Therefore, transmittance $I(x)/I_0$ becomes 0.74 when the pulse light LP11 proceeds by 0.3 μm. That is, 26% of the pulse light LP11 is absorbed by the n-type silicon layer 94, and the remaining pulse light LP11 reaches the p-type silicon layer 93.

Based on the above principle, the depth direction of the inspection object can more particularly be inspected by properly selecting the wavelength of the pulse light LP11 with which the solar cell 90 of the inspection object is irradiated.

As described above, the depletion layer is formed in the pn-junction 97 for the solar cell 90 in FIG. 3. Assuming that the wavelength of the pulse light LP11 is the wavelength that can reach the pn-junction 97, the electromagnetic wave pulse LT1 generated according to the depletion layer and the PL light PL1 generated by the photocarriers excited in the n-type silicon layer 94 can be detected.

In this case, in the case that only the intensity of the electromagnetic wave pulse LT1 is abnormal in a specific inspection part, it can be estimated that the defect exists near the depletion layer of the inspection part. In the case that only the intensity of the PL light PL1 is abnormal, it can be estimated that the defect exists in the n-type silicon layer 94 (near the surface of the solar cell 90) in the inspection part.

For example, for the n-type silicon layer 94 having the thickness of 0.3 μm, the wavelength of the pulse light LP11 that can reach the depletion layer may be set to 365 nm. This is because, as described above, 95% of the light having the wavelength of 365 nm is absorbed when the light proceeds in the crystalline silicon layer by 0.3 μm. In the present invention, the depth (invasion length) at which the light can reach is set to the depth (that is, the depth when 63% of the light is absorbed) in which the transmittance $I(x)/I_0$ becomes 0.37.

On the other hand, when the solar cell 90 is irradiated with the pulse light LP11 that can reach a portion deeper than the depletion layer, namely, the p-type silicon layer 93, the photocarriers can be excited in both the n-type silicon layer 94 and the p-type silicon layer 93. Accordingly, the PL light PL1 depending on the photocarriers generated in both the n-type silicon layer 94 and the p-type silicon layer 93 can be detected.

In the case that the solar cell 90 is irradiated with the pulse light LP11 that can arrive at the p-type silicon layer 93, it can be estimated that the defect exists near the depletion layer in a specific inspection part when only the intensity of the electromagnetic wave pulse LT1 is abnormal in the specific inspection part. In the case that only the intensity of the PL light PL1 is abnormal, it can be estimated that the defect exists in the n-type silicon layer 94 or p-type silicon layer 93 in the inspection part.

For example, for the n-type silicon layer 94 having the thickness of 0.3 μm, the wavelength of the pulse light LP11 that can reach the portion deeper than the depletion layer may be set to 500 nm. This is because, as described above, only 26% of the light having the wavelength of 500 nm is absorbed when the light proceeds in the crystalline silicon layer by 0.3 μm.

The inspection position setting part 29 sets an area irradiated with the pulse light LP11 in order to acquire the electromagnetic wave intensity distribution or the PL light intensity distribution. The inspection position setting part 29 displays an area designating screen on the monitor 17, and receives a designation input performed by an operator through the operation input part 18. The inspection position setting part 29 sets the area irradiated with the pulse light LP11 based on the designation input. The control part 16 controls the irradiation part 12 and the stage moving mechanism 15 such that the area set in the above manner is scanned with the pulse light LP11.

The monitor 17 and the operation input part 18 are connected to the control part 16. The monitor 17 is a display device such as a liquid crystal display, and displays various pieces of image information to the operator. For example, the image of the light receiving surface 91S of the solar cell 90 photographed with the CCD camera, the time waveform of the electromagnetic wave pulse LT1 restored by the time waveform restoration part 21, and an analysis result of the electromagnetic wave pulse analysis part 23 are displayed on the monitor 17. Additionally, the electromagnetic wave intensity distribution image generated by the electromagnetic wave intensity distribution image generation part 25, the PL light intensity distribution image generated by the PL light intensity distribution image generation part 27, the synthetic image generated by the image synthesis part 28, and the screen on which the inspection position setting part 29 receives the designation manipulation input are displayed on the monitor 17. A GUI (Graphical User Interface) screen necessary to set an inspection condition is properly displayed on the monitor 17.

The operation input part 18 is constructed with various input devices such as a mouse and a keyboard. The operator can perform various manipulation inputs to the inspection apparatus 100 through the operation input part 18. When a touch panel is used as the monitor 17, the monitor 17 may also act as the operation input part 18.

The configuration of the inspection apparatus 100 is described above. A specific example of the inspection of the solar cell 90, which can be performed in the inspection apparatus 100, will be described below.

1.2. Inspection of Solar Cell

1.2.1. Inspection Example 1

Figure 6:
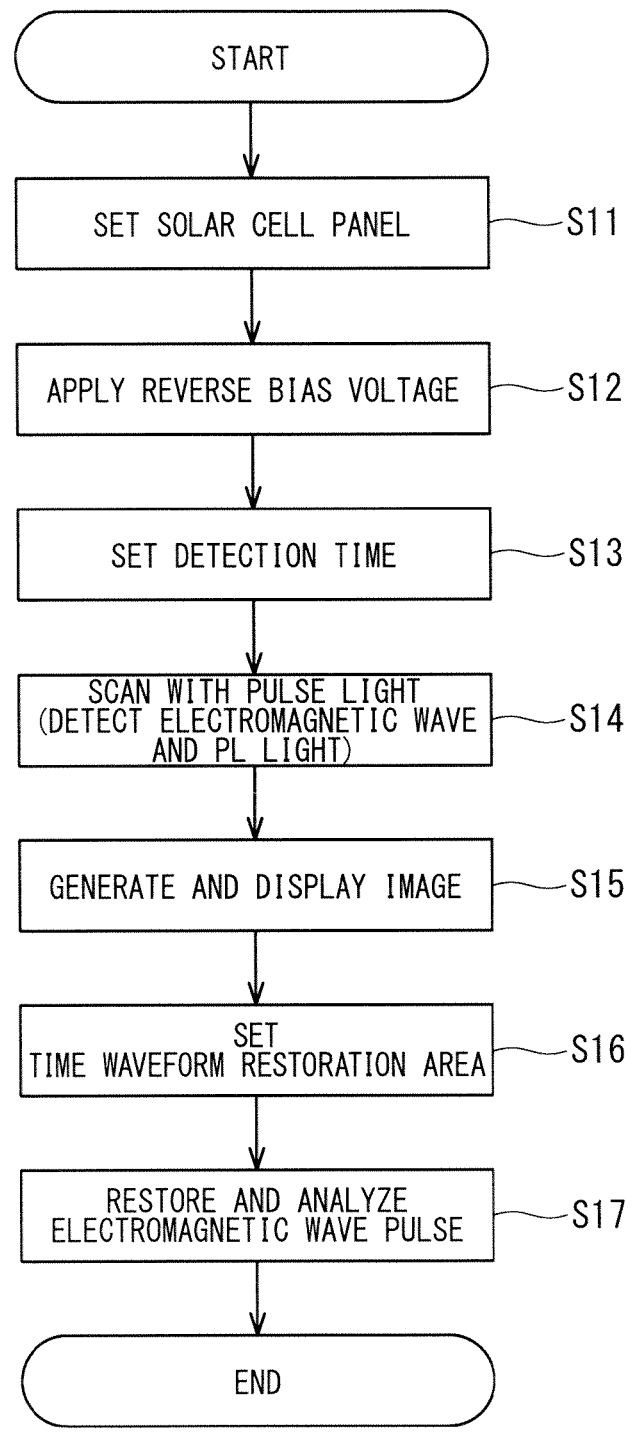
FIG. 6 is a flowchart illustrating an inspection example 1 of the solar cell.

FIG. 6 is a flowchart illustrating an inspection example 1 of the solar cell 90. Hereinafter, unless otherwise noted, it is assumed that each operation of the inspection apparatus 100 is performed under the control of the control part 16. Depending on a content of each process, plural processes may concurrently be performed, or the order of plural processes may properly be changed.

The solar cell 90 as the inspection target is placed on the stage 11 (Step S11). At this point, as described above, the solar cell 90 is placed such that the light receiving surface 91S (that is, the principal surface on the side on which sunlight is received in the use state of the solar cell 90) is irradiated with the pulse light LP11.

When the solar cell 90 is placed, the reverse bias voltage applying circuit 99 is connected to the backside electrode 92 and light receiving surface electrode 96 of the solar cell 90, and the reverse bias voltage is applied (Step S12). In the case that the reverse bias voltage is not applied, Step S12 can be eliminated.

Detection time of the electromagnetic wave pulse LT1 detected by the electromagnetic wave detection part 13 is set (Step S13). Specifically, the control part 16 controls the delay stage 131a, whereby the position of the turning back mirror 10M is adjusted such that the time the probe light LP12 reaches the detector 132 is fixed to a required detection time. The detection time is set such that the detected electromagnetic wave intensity increases as much as possible, which allows enhancement of an S/N ratio.

When the detection time is set, the stage moving mechanism 15 is driven to move the solar cell 90 in the two-dimensional plane. Therefore, the inspection object area is scanned with the pulse light LP11 (Step S14). The PL light detection part 14 detects the PL light PL1 generated at each position irradiated with the pulse light LP11 at the same time as the detector 132 detects the electric field intensity of the electromagnetic wave pulse LT1 emitted at each position irradiated with the pulse light LP11.

In Step S14, when the electric field intensity of the electromagnetic wave pulse LT1 at each position irradiated with the pulse light LP11 and the light intensity of the PL light PL1 are acquired, the electromagnetic wave intensity distribution image generation part 25 and the PL light intensity distribution image generation part 27 generate the electromagnetic wave intensity distribution image and the PL light intensity distribution image. The electromagnetic wave intensity distribution image and the PL light intensity distribution image are displayed on the identical screen of the monitor 17 (Step S15). In Step S15, the synthetic image in which the electromagnetic wave intensity distribution image and the PL light intensity distribution image are synthesized may be generated by the image synthesis part 28, and displayed on the monitor 17.

Figure 8:
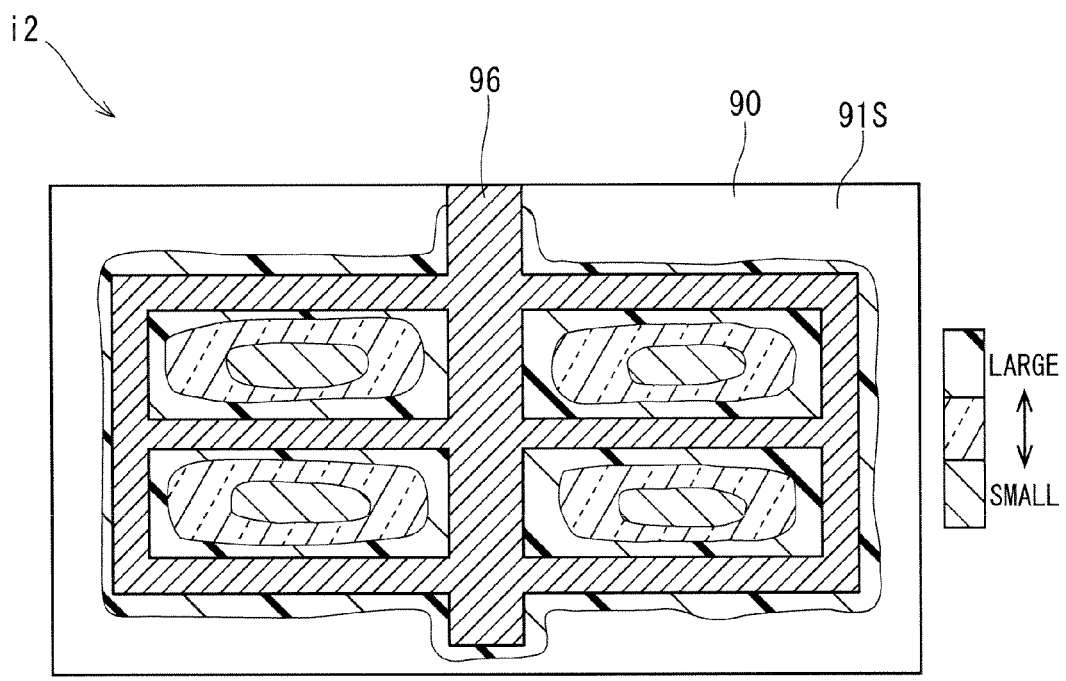
FIG. 8 is a view illustrating a PL light intensity distribution image.

FIG. 7 is a view illustrating an electromagnetic wave intensity distribution image i1. FIG. 8 is a view illustrating a PL light intensity distribution image i2. According to the electromagnetic wave intensity distribution image i1, the electric field intensity distribution in the solar cell 90 can easily be understood. According to the PL light intensity distribution image i2, the electric field intensity distribution in the solar cell 90 can easily be understood.

Referring back to FIG. 6, when the display of each image is completed, the inspection position setting part 29 receives the designation of the area (time waveform restoration inspection area) where the time waveform of the electromagnetic wave pulse LT1 is restored to perform the inspection (Step S16). In Step S16, the operator designates the area where the detailed inspection is required through the operation input part 18 while checking the electromagnetic wave intensity distribution image i1, the PL light intensity distribution image i2, or the synthetic image thereof displayed on the monitor 17. The inspection position setting part 29 sets the designated area to the time waveform restoration inspection area.

The time waveform restoration inspection area may automatically be set. For example, a reference value range where the electromagnetic wave intensity or the PL light intensity is normal is previously decided, and the inspection position setting part 29 may automatically set the position where the electromagnetic wave intensity or PL light intensity out of the reference value range is detected to the time waveform restoration inspection area.

The inspection apparatus 100 irradiates the time waveform restoration inspection area set in Step S16 with the pulse light LP11 again, and restores and analyzes the electromagnetic wave pulse LT1 (Step S17). The restoration and analysis of the electromagnetic wave pulse LT1 will be described with reference to FIG. 9.

Figure 9:
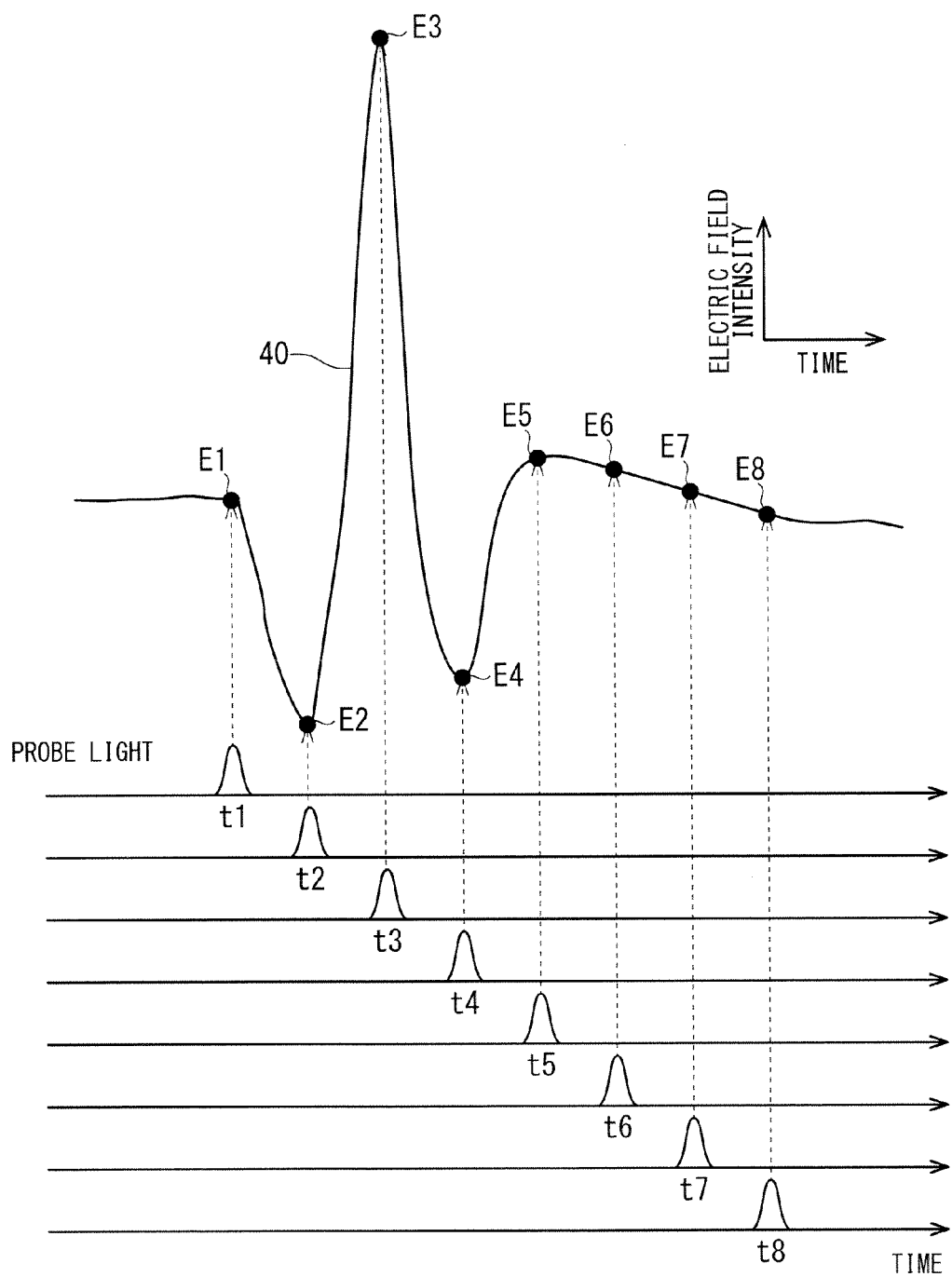
FIG. 9 is a view illustrating an example of a time waveform of an electromagnetic wave pulse restored by a time waveform restoration part.

FIG. 9 is a view illustrating an example of a time waveform 40 of the electromagnetic wave pulse LT1 restored by the time waveform restoration part 21. In a graph of FIG. 9, a horizontal axis indicates the time and a vertical axis indicates the electric field intensity. In FIG. 9, plural pieces of probe light LP12 are conceptually indicated below the graph illustrating the time waveform 40. The plural pieces of probe light LP12 differ from one another in the time (t1 to t8) the probe light LP12 reaches the detector 132 because the probe light LP12 is delayed by the delay stage 131a.

When the solar cell 90 is irradiated with the pulse light LP11, the electromagnetic wave pulse LT1 having the time waveform 40 in FIG. 9 repeatedly reaches the detector 132 with a period corresponding to a pulse period of the pulse light LP11.

For example, in the case that the delay stage 131a is adjusted such that the probe light LP12 reaches the detector 132 at a detection time t1, the detector 132 detects the electric field intensity having a value E1. When the detection time is delayed to each of t2 to t8 by adjusting the delay stage 131a, the electromagnetic wave detection part 13 detects the electric field intensity having each of values E2 to E8. The detection time is finely changed by controlling the delay stage 131a, whereby the electric field intensity of the electromagnetic wave pulse LT1 is measured at each detection time (each phase). The time waveform restoration part 21 plots the acquired value of the electric field intensity on the graph along the time axis to restore the time waveform 40 of the electromagnetic wave pulse LT1.

The time waveform 40 includes information on each of the generation, movement, and disappearance processes of the photoexcited carrier according to the irradiation of the solar cell 90 with the pulse light LP11. That is, dynamics of the photoexcited carrier can be analyzed by acquiring the time waveform 40. Therefore, the defect (for example, a lattice defect of a crystal) or the impurity of the solar cell 90 can more particularly be analyzed.

In Step S13, the time waveform is restored on a trial basis, and the detection time may be set based on the time waveform. For example, the time waveform of the electromagnetic wave pulse LT1 emitted in response to the irradiation of the inspection object area with the pulse light LP11 can be restored at any position in the inspection object area by the method described in FIG. 9. The time (phase) the electric field intensity increases can easily be understood from the restored time waveform. Therefore, the detection time can properly be set such that the S/N ratio is sufficiently enhanced.

Figure 10:
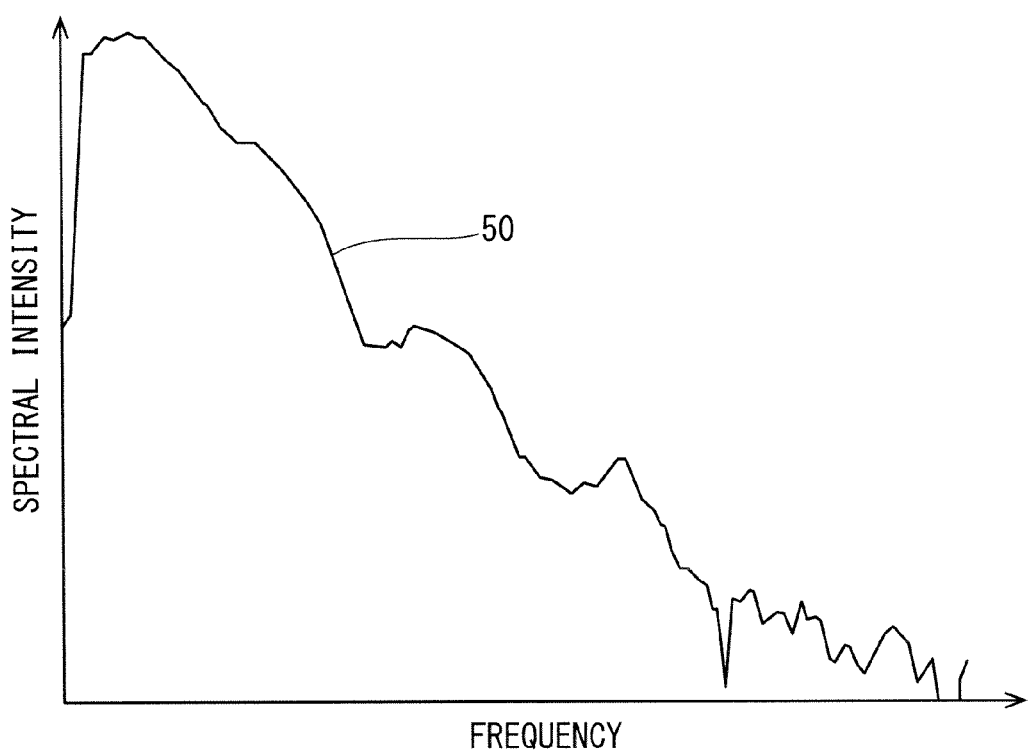
FIG. 10 is a view illustrating an example of a spectral distribution of the electromagnetic wave pulse.

FIG. 10 is a view illustrating an example of a spectral distribution 50 of the electromagnetic wave pulse LT1. In FIG. 10, the vertical axis indicates a spectral intensity and the horizontal axis indicates the frequency. The electromagnetic wave pulse analysis part 23 performs a Fourier transform to convert a time region into a frequency space, whereby the spectral distribution 50 shown in FIG. 10 may be acquired from the time waveform 40 shown in FIG. 9. Information on a physical property in the inspection object area can more particularly be analyzed by acquiring the spectral distribution 50.

As described above, in the inspection apparatus 100 of the first preferred embodiment, the data of the electromagnetic wave intensity and the data of the PL light intensity can be acquired using the pulse light LP11 emitted from the identical light source (femtosecond laser 121). Therefore, it is not necessary that the light sources be separately prepared in order to acquire the data of the electromagnetic wave intensity and the data of the PL light intensity. Accordingly, a cost increase and enlargement of the apparatus can be constrained. Additionally, inspection cost can be constrained, and the enlargement of an occupation area of the inspection apparatus 100 can be constrained.

According to the inspection example 1 in FIG. 6, the data of the electromagnetic wave intensity and the data of the PL light intensity can simultaneously be collected by scanning the solar cell 90 with the identical pulse light LP11 once. Accordingly, the data can efficiently be collected. Alternatively, the data of the electromagnetic wave intensity and the data of the PL light intensity may be separately collected by scanning the inspection object area with the pulse light LP11 twice.

The electromagnetic wave pulse LT1 is generated in proportion to the movement of the photoexcited carrier generated in response to the irradiation of the solar cell 90 with the pulse light LP11, namely, the time differentiation of the photocurrent. On the other hand, the PL light PL1 is generated by recombining the electron and hole that are of the photoexcited carriers generated by the irradiation of the solar cell 90 with the pulse light LP11. Thus, in the inspection apparatus 100, the solar cell 90 can be inspected from different angles by measuring two kinds of physical phenomena that differ from each other in a principle of the generation.

In the inspection in which the time waveform is restored, because the delay stage 131a is adjusted, it takes a relatively long time to acquire the data of the electromagnetic wave intensity. On the other hand, in the inspection example 1, the area of the inspection in which the time waveform is restored is restricted based on the electromagnetic wave intensity distribution and the PL light intensity distribution, so that the solar cell 90 can efficiently be inspected.

1.2.2. Inspection Example 2

Figure 11:
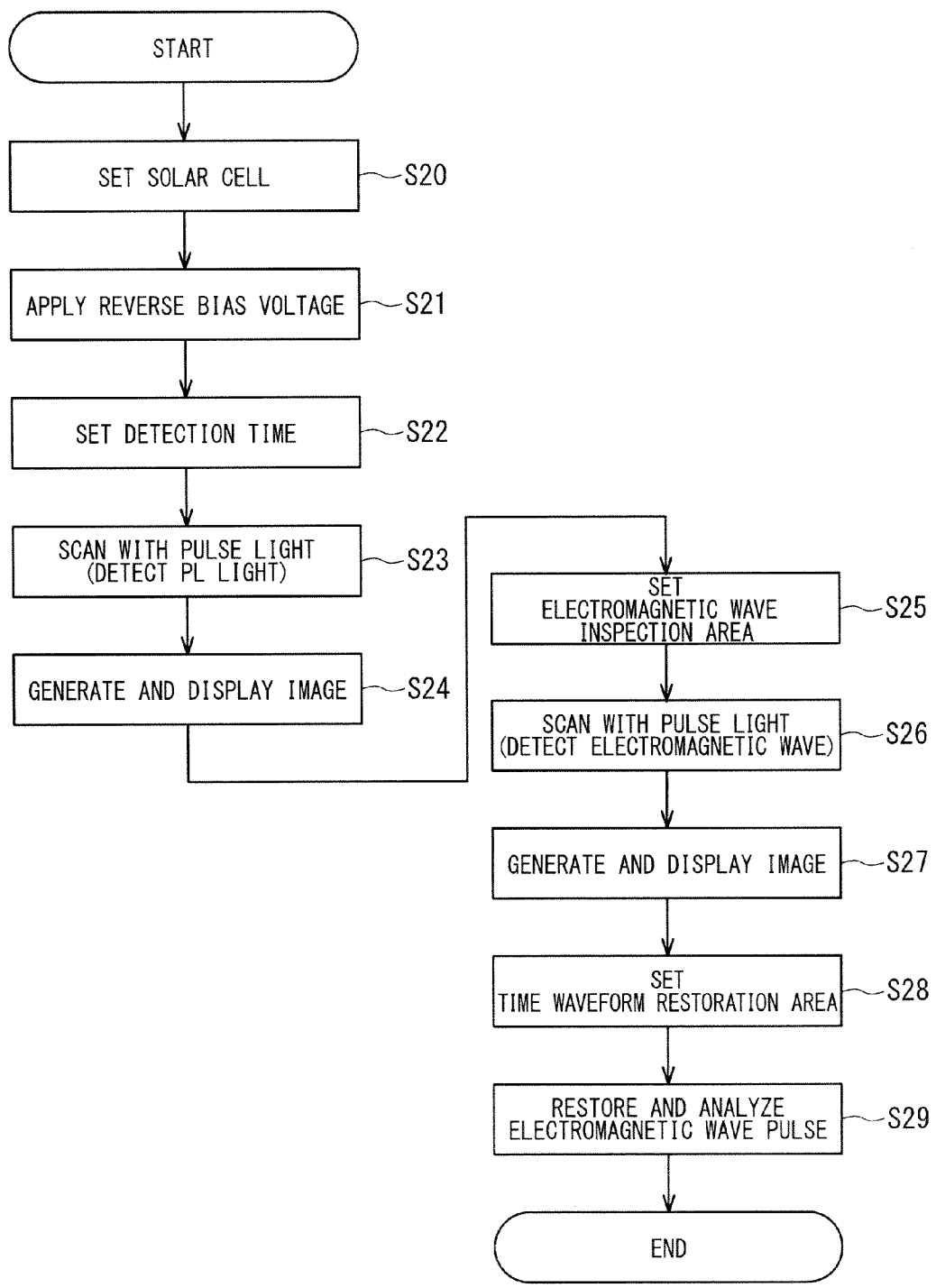
FIG. 11 is a flowchart illustrating an inspection example 2 of the solar cell.

FIG. 11 is a flowchart illustrating an inspection example 2 of the solar cell 90. In a flow of the inspection example 2 in FIG. 11, because the placement of the solar cell 90 (Step S20), the application of the reverse bias voltage (Step S21), and the setting of the detection time (Step S22) are similar to Steps S11 to S13 of the inspection example 1 in FIG. 6, the description is omitted.

When the setting of the detection time is completed in Step S22, the inspection apparatus 100 detects only the intensity data of the PL light PL1 that is generated from the portion irradiated with the pulse light LP11 in the solar cell 90 in scanning the inspection object area with the pulse light LP11 (Step S23). Based on the PL light intensity data acquired in Step S23, the PL light intensity distribution image is generated by the PL light intensity distribution image generation part 27, and displayed on the monitor 17 (Step S24).

The inspection position setting part 29 receives the designation of the area where the electric field intensity of the electromagnetic wave pulse LT1 should be acquired, and sets the designated area to the electromagnetic wave inspection area (Step S25). Specifically, the operator manipulates to input to designate the electromagnetic wave inspection area while checking the PL light intensity distribution image displayed on the monitor 17. According to the operation, the inspection position setting part 29 sets the electromagnetic wave inspection area.

In Step S25, the electromagnetic wave inspection area may automatically be set. For example, the reference value range where the PL light intensity is normal is previously decided. The electromagnetic wave inspection area is automatically set so as to include the position where the PL light intensity out of the reference value range is detected in the inspection object area. In this case, the inspection position setting part 29 acts as a determination part that determines whether the PL light intensity satisfies a predetermined reference value or not.

When the electromagnetic wave inspection area is set, the inspection apparatus 100 scans the electromagnetic wave inspection area with the pulse light LP11 to detect the electric field intensity of the emitted electromagnetic wave pulse LT1 (Step S26). It is considered that the area where the PL light intensity is abnormal is a defect candidate area or an impurity containing area. The area where the PL light intensity is abnormal is continuously inspected as the electromagnetic wave inspection area, which allows more useful information to be acquired. Based on the collected electromagnetic wave intensity data, the electromagnetic wave intensity distribution image is generated by the electromagnetic wave intensity distribution image generation part 25, and displayed on the monitor 17 (Step S27).

When the electromagnetic wave intensity distribution image is displayed on the monitor 17, the inspection position setting part 29 sets time waveform restoration analysis area (Step S28). The time waveform is restored and analyzed in the time waveform restoration analysis area (Step S29). Because Steps S28 and S29 are similar to Steps S16 and S17 of the inspection example 1 shown in FIG. 6, the detailed description is omitted.

In order to acquire the highly-reliable electromagnetic wave intensity data, it is necessary to repeatedly irradiate the identical place with the pulse light LP11 a predetermined number of times. For this reason, generally the acquisition of the electromagnetic wave intensity is longer than the acquisition of the PL light intensity in a measurement time. In the inspection example 2 of FIG. 11, the range (electromagnetic wave inspection area) where the electromagnetic wave intensity is acquired is narrowed based on the previously-acquired PL light intensity distribution of the inspection object area. Therefore, the inspection object area in the solar cell 90 can efficiently be inspected.

During Step S23 (that is, during the scan in acquiring the PL light intensity data), in the case that the acquired PL light intensity data is out of the predetermined reference value range when a certain place is irradiated with the pulse light LP11, the electromagnetic wave intensity may immediately be acquired in the place. In this case, because the PL light intensity data of the inspection object area and the electromagnetic wave data of the specific place can be obtained with the one-time scan, the efficient inspection can be achieved.

In the inspection example 2 of FIG. 11, the electromagnetic wave intensity data is collected in the electromagnetic wave inspection area after the PL light intensity data is collected in the inspection object area. Alternatively, after the electromagnetic wave intensity data is collected in the inspection object area, the PL light intensity data may be collected in the area narrower than the inspection object area.

The electromagnetic wave inspection area where the electromagnetic wave intensity is acquired is not necessarily included in the area (PL light inspection area) where the PL light intensity is acquired. For example, the electromagnetic wave inspection area and the PL light inspection area may be set so as to partially overlap with each other or so as not to overlap with each other.

The electromagnetic wave inspection area, the PL light inspection area, and the electromagnetic wave restoration inspection area may be set by the inspection position setting part 29 before the inspection. In this case, for example, the operator may designate each inspection area on the image photographed with the CCD camera.

2. Second Preferred Embodiment

Figure 12:
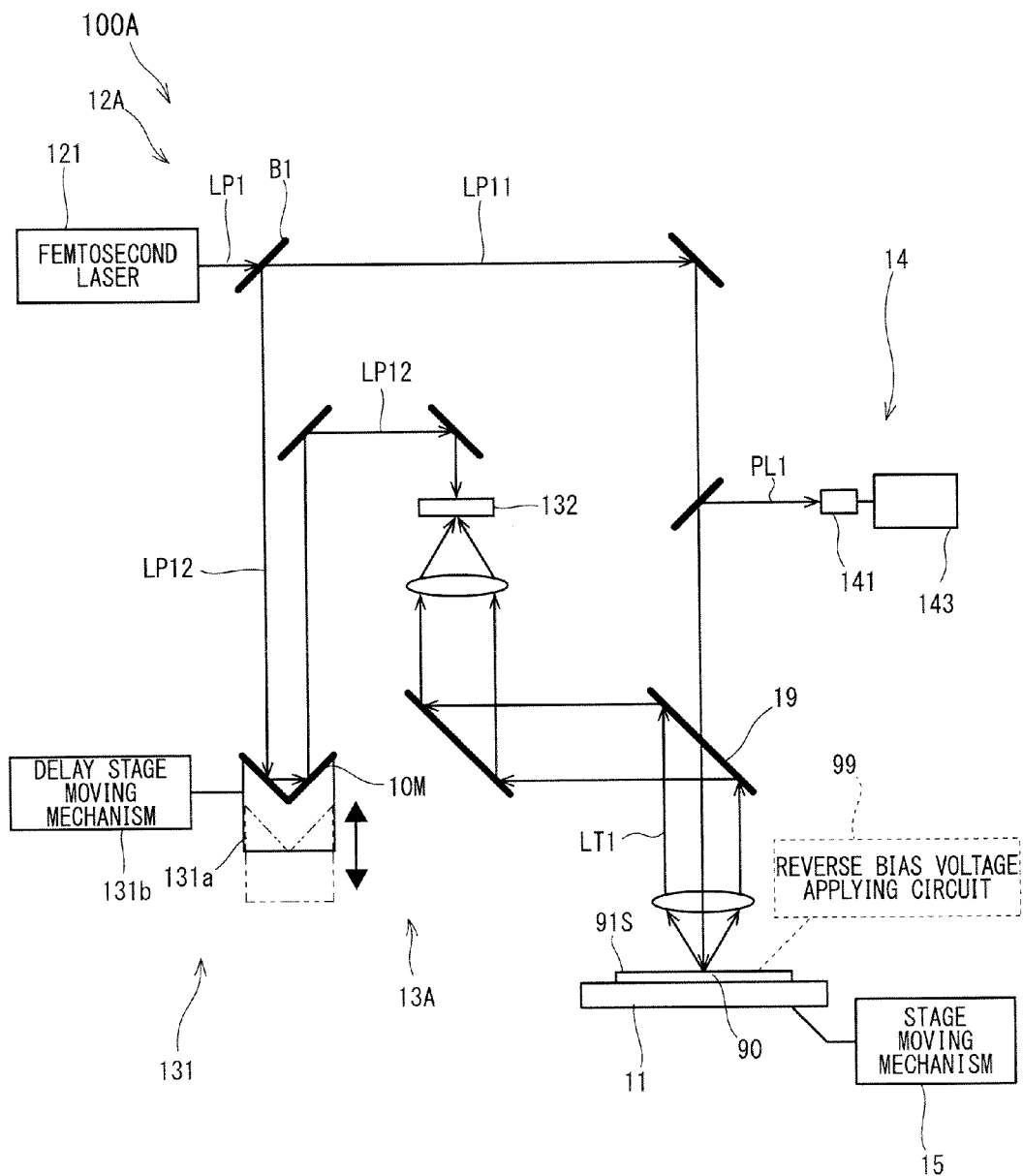
FIG. 12 is a schematic diagram illustrating configurations of an irradiation part and a detection part, which are included in a photo device inspection apparatus according to a second preferred embodiment.

FIG. 12 is a schematic diagram illustrating configurations of an irradiation part 12A and an electromagnetic wave detection part 13A, which are included in an inspection apparatus 100A according to a second preferred embodiment. In the following description, the component having a function similar to that of the inspection apparatus 100 of the first preferred embodiment is designated by the identical numeral, and the description thereof is omitted.

As illustrated in FIG. 12, in the inspection apparatus 100A, the pulse light LP11 split by the beam splitter B1 is transmitted through a transparent conductive substrate (ITO) 19, and is perpendicularly incident to the light receiving surface 91S of the solar cell 90. In the electromagnetic wave pulse LT1 emitted from the solar cell 90 in response to the irradiation of the solar cell 90 with the pulse light LP11, the electromagnetic wave pulse LT1 emitted from the side of the light receiving surface 91S is reflected by the transparent conductive substrate 19, collected by a lens, and is incident to the detector 132.

In the inspection apparatus 100A, the PL light PL1 emitted from the solar cell 90 in response to the irradiation of the solar cell 90 with the pulse light LP11 passes through the transparent conductive substrate 19, and is incident to the PL light detection part 14. The placement mode of the PL light detection part 14 shown in FIG. 12 is illustrated by way of example, but the PL light detection part 14 is not limited to the placement mode shown in FIG. 12.

In the inspection apparatus 100A, similarly to the inspection apparatus 100 of the first preferred embodiment, the electromagnetic wave pulse LT1 emitted from the solar cell 90 can be detected. Additionally, the PL light PL1 emitted from the solar cell 90 in response to the irradiation of the solar cell 90 with the pulse light LP11 can be detected by the PL light detection part 14.

3. Third Preferred Embodiment

Figure 13:
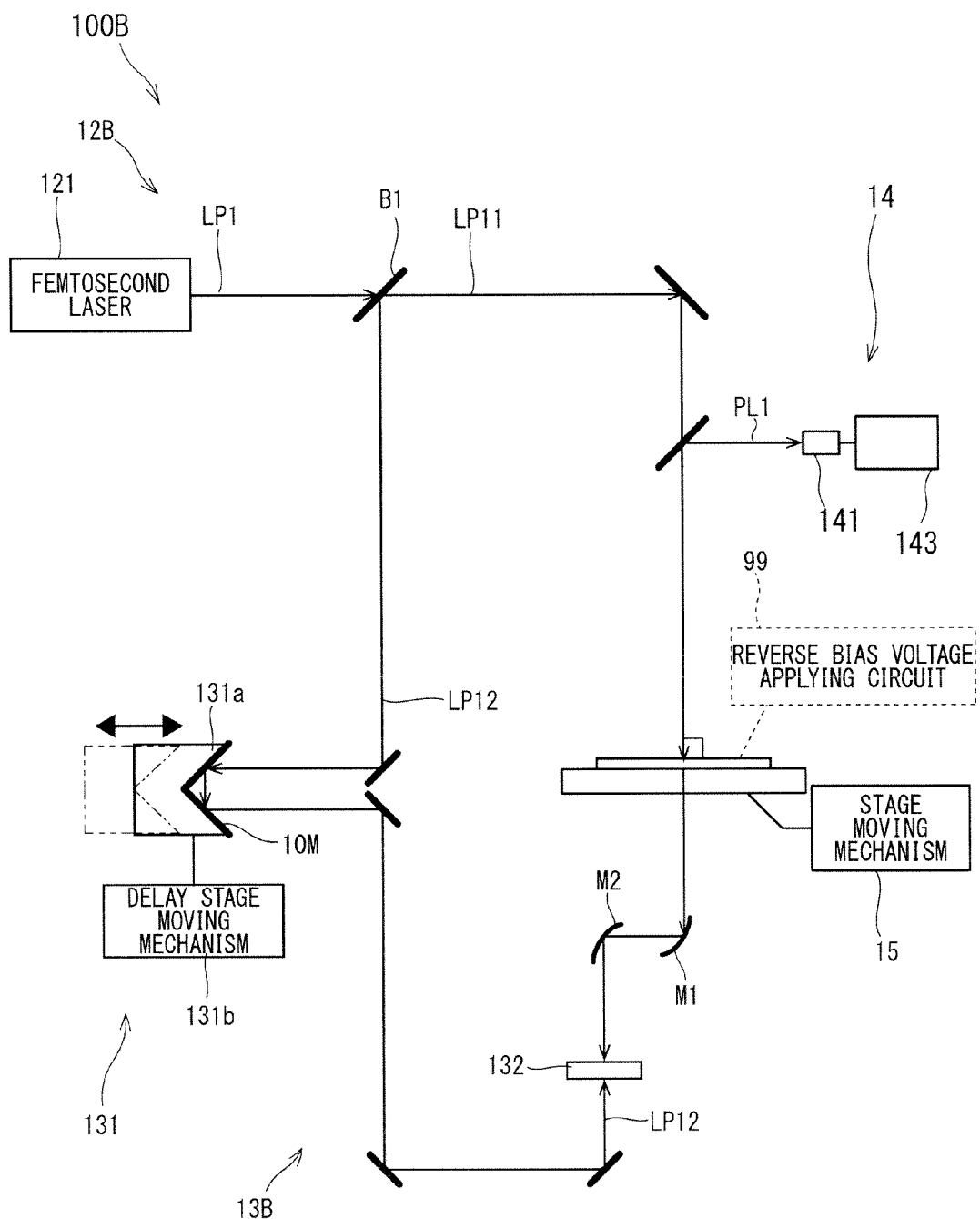
FIG. 13 is a schematic diagram illustrating configurations of an irradiation part and a detection part, which are included in a photo device inspection apparatus according to a third preferred embodiment.

FIG. 13 is a schematic diagram illustrating configurations of an irradiation part 12B and an electromagnetic wave detection part 13B, which are included in an inspection apparatus 100B according to a third preferred embodiment. In the inspection apparatus 100B, the pulse light LP11 split by the beam splitter B1 is perpendicularly incident to the light receiving surface 91S of the solar cell 90. In the electromagnetic wave pulse LT1 emitted from the solar cell 90 in response to the irradiation of the solar cell 90 with the pulse light LP11, the electromagnetic wave pulse LT1 emitted from the back side of the light receiving surface 90S (that is, transmitted through the solar cell 90) is incident to the detector 132 through the parabolic mirrors M1 and M2.

In the inspection apparatus 100B, the PL light PL1 emitted in the direction coaxial with the pulse light LP11 incident to the solar cell 90 is detected by the PL light detection part 14. The placement mode of the PL light detection part 14 shown in FIG. 13 is illustrated by way of example, but the PL light detection part 14 is not limited to the placement mode shown in FIG. 13.

In the inspection apparatus 100B, the electromagnetic wave pulse LT1 emitted from the solar cell 90 can be detected. Additionally, the PL light PL1 generated in the solar cell 90 in response to the irradiation of the solar cell 90 with the pulse light LP11 can be detected by the PL light detection part 14.

While the invention has been shown and described in detail, the foregoing description is in all aspects illustrative and not restrictive. It is therefore understood that numerous modifications and variations can be devised without departing from the scope of the invention.

What is claimed is:

1. An inspection apparatus that inspects an inspection object including a semiconductor device or a photo device, the inspection apparatus comprising:
   an irradiation part that irradiates said inspection object with pulse light emitted from a femtosecond laser;
   an electromagnetic wave detection part that detects an electromagnetic wave emitted from said inspection object in response to the irradiation of said inspection object with said pulse light; and
   a PL light detection part that detects photoluminescence light emitted from said inspection object in response to the irradiation of said inspection object with said pulse light generating said electromagnetic wave from said inspection object,
   said electromagnetic wave detection part comprising:
      a detector that detects an electric field intensity of said electromagnetic wave by receiving probe light emitted from said femtosecond laser; and
      a delay part that that delays a time said probe light is incident to said detector relative to a time said electromagnetic wave is incident to said detector,
   said inspection apparatus further comprising a time waveform restoration part that restores a time waveform of said electromagnetic wave based on an electric field intensity of said electromagnetic wave detected by operating a delay part.

2. The inspection apparatus according to claim 1, wherein said pulse light is light that can reach a portion deeper than a depletion layer of said inspection object.

3. The inspection apparatus according to claim 1, wherein said pulse light is light that is absorbed by a depletion layer in said inspection object.

4. The inspection apparatus according to claim 1, further comprising a scanning mechanism that scans an inspection object area in said inspection object with said pulse light.

5. The inspection apparatus according to claim 4, further comprising an electromagnetic wave intensity distribution image generation part that generates an electromagnetic wave intensity distribution image indicating an intensity distribution of said electromagnetic wave generated in said inspection object area.

6. The inspection apparatus according to claim 4 further comprising a PL light intensity distribution image generation part that generates a PL light intensity distribution image indicating an intensity distribution of said photoluminescence light generated in said inspection object area.

7. The inspection apparatus according to claim 6, further comprising:
   an electromagnetic wave intensity distribution image generation part that generates an electromagnetic wave intensity distribution image indicating an intensity distribution of said electromagnetic wave generated in said inspection object area; and
   an image synthesis part that synthesizes said PL light intensity distribution image and said electromagnetic wave intensity distribution.

8. The inspection apparatus according to claim 1, further comprising an inspection position setting part that sets a position where said irradiation part irradiates said inspection object with said pulse light in order to restore said time waveform.

9. The inspection apparatus according to claim 4, further comprising a determination part that determines whether an intensity of said photoluminescence light detected by said PL light detection part satisfies a predetermined reference value, wherein
said scanning mechanism scans an area where said reference value is not satisfied with said pulse light, and
said electromagnetic wave detection part detects an electromagnetic wave generated by the scan.

10. An inspection method for inspecting an inspection object including a semiconductor device or a photo device, the inspection method comprising the steps of:
(a) irradiating said inspection object with pulse light emitted from a femtosecond laser;
(b) detecting an electromagnetic wave emitted from said inspection object in response to the irradiation of said inspection object with said pulse light; and
(c) detecting photoluminescence light emitted from said inspection object in response to the irradiation of said inspection object with said pulse light generating said electromagnetic wave from said inspection object, wherein
said step (b) includes:
(b-1) detecting an electric field intensity of said electromagnetic wave by a detector by receiving probe light emitted from said femtosecond laser; and
(b-2) delaying a time said probe light is incident to said detector relative to a time said electromagnetic wave is incident to said detector,
said inspection method further comprising the step of restoring a time waveform of said electromagnetic wave based on an electric field intensity of said electromagnetic wave detected by said step (b-2).

11. The inspection method according to claim 10, wherein said step (a) includes
(a-1) a step of scanning an inspection object area of said inspection object with said pulse light.

12. An inspection apparatus that inspects an inspection object including a semiconductor device or a photo device, the inspection apparatus comprising:
an irradiation part that irradiates said inspection object with pulse light emitted from a light source;
an electromagnetic wave detection part that detects an electromagnetic wave emitted from said inspection object in response to the irradiation of said inspection object with said pulse light;
a PL light detection part that detects photoluminescence light emitted from said inspection object in response to the irradiation of said inspection object with said pulse light generating said electromagnetic wave from said inspection object;
a scanning mechanism that scans an inspection object area in said inspection object with said pulse light; and
a determination part that determines whether an intensity of said photoluminescence light detected by said PL light detection part satisfies a predetermined reference value, wherein
said scanning mechanism scans an area where said reference value is not satisfied with said pulse light, and
said electromagnetic wave detection part detects an electromagnetic wave generated by the scan.

* * * * *